(12) United States Patent
Schneider et al.

(10) Patent No.: US 9,408,940 B2
(45) Date of Patent: *Aug. 9, 2016

(54) ODOR-CONTROLLING BODILY FLUID ABSORBER

(71) Applicants: David J. Schneider, Union, KY (US); Charles A. Schneider, Villa Hills, KY (US)

(72) Inventors: David J. Schneider, Union, KY (US); Charles A. Schneider, Villa Hills, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/867,294

(22) Filed: Apr. 22, 2013

(65) Prior Publication Data

US 2013/0236414 A1   Sep. 12, 2013

Related U.S. Application Data

(63) Continuation of application No. 12/710,704, filed on Feb. 23, 2010, now Pat. No. 8,425,890.

(60) Provisional application No. 61/154,909, filed on Feb. 24, 2009.

(51) Int. Cl.
*A61L 15/20* (2006.01)
*A61L 15/46* (2006.01)
*A61L 101/36* (2006.01)
*A61F 13/84* (2006.01)

(52) U.S. Cl.
CPC .............. *A61L 15/20* (2013.01); *A61F 13/8405* (2013.01); *A61L 15/46* (2013.01); *A61L 2300/406* (2013.01)

(58) Field of Classification Search
CPC ..... A61F 13/8405; A61L 15/20; A61L 15/46; A61L 2300/406; A61L 2300/202; C07C 311/15
USPC ......... 514/117, 602, 604; 424/76.6, 443, 431, 424/445, 447; 564/84–88
See application file for complete search history.

(56) References Cited

U.S. PATENT DOCUMENTS

| 4,892,598 | A | 1/1990 | Stevens et al. |
| 4,959,060 | A | 9/1990 | Shimomura et al. |
| 6,296,841 | B1 | 10/2001 | Schneider |
| 6,667,030 | B1 | 12/2003 | Schneider |
| 6,743,420 | B2 | 6/2004 | Schneider |
| 7,018,490 | B2 | 3/2006 | Hansen et al. |
| 7,371,368 | B2 | 5/2008 | Schneider et al. |
| 7,465,829 | B2 | 12/2008 | Schneider et al. |
| 7,513,915 | B2 | 4/2009 | Schneider et al. |
| 7,560,592 | B2 | 7/2009 | Schneider et al. |
| 7,629,492 | B2 | 12/2009 | Schneider et al. |
| 2004/0062742 | A1 | 4/2004 | Winston et al. |
| 2004/0265265 | A1 | 12/2004 | Schneider et al. |
| 2005/0287109 | A1 | 12/2005 | Schneider et al. |
| 2006/0075975 | A1 | 4/2006 | Schneider et al. |
| 2006/0276672 | A1 | 12/2006 | Schneider et al. |
| 2010/0041761 | A1 | 2/2010 | Schneider et al. |

FOREIGN PATENT DOCUMENTS

| EP | 1 034 799 A1 | 9/2000 |
| WO | WO 94/01069 | 1/1994 |
| WO | WO 00/51653 | 9/2000 |

OTHER PUBLICATIONS

Supplementary European Search Report for Application No./Patent No. 10746707.8 — 2103 / 2400995 PCT US2010025064; Date of completion of the search: Aug. 1, 2012; Place of search: Munich.

*Primary Examiner* — Alma Pipic
(74) *Attorney, Agent, or Firm* — Richard M. Klein; Fay Sharp LLP (57) ABSTRACT

An odor-controlling bodily fluid absorbent member comprises (a) an absorbent material or substrate; and (b) a halo active aromatic sulfonamide compound of Formula (I):

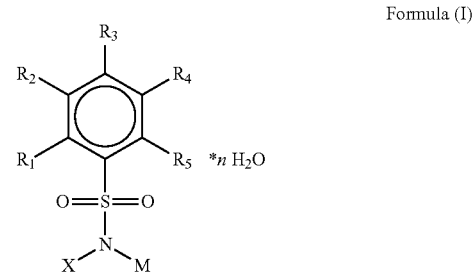

wherein $R_1$, $R_2$, $R_3$, $R_4$, $R_5$, X, M, and n are as described herein; and wherein at least one of $R_1$, $R_2$, $R_3$, $R_4$, and $R_5$ is not hydrogen. The absorbent member effectively controls odor arising from various body fluids.

20 Claims, 3 Drawing Sheets

ODOR-CONTROLLING BODILY FLUID ABSORBER

The present application is a continuation of U.S. patent application Ser. No. 12/710,704, filed Feb. 23, 2010, now U.S. Pat. No. 8,425,890, which claims priority from U.S. Provisional Patent Application Ser. No. 61/154,909, filed on Feb. 24, 2009. The disclosure of these applications are hereby fully incorporated by reference herein.

BACKGROUND

The present disclosure relates to bodily fluid absorbent members having odor control characteristics.

Absorbent members, such as pads, find widespread use in absorbing body or bodily fluids in articles such as catamenial devices, diapers (both for babies and individuals with incontinence problems), sanitary napkins, tampons, wound dressings, and bandages. Such absorbent members may incorporate super absorbent polymers (which absorb many times their own weight of fluid) or other fibrous materials, such as cotton, wood pulp, and paper. The bodily fluids absorbed by such absorbent members may include blood, pus, sweat, semen, secretions, menstrual discharge, urine, and fecal matter.

The bodily fluid may have an unpleasant odor due to odor-causing molecules which may be aliphatic, aromatic, or heterocyclic compounds containing oxygen, sulfur, or nitrogen. The odor-causing molecules can be masked using a more pleasant smelling molecule, such as a perfume, or can be encapsulated. However, it would be desirable to alter, neutralize, and/or destroy the odor-causing molecule instead. It would also be beneficial to provide improved bodily fluid absorbent members having enhanced odor control properties.

BRIEF DESCRIPTION

Disclosed herein, in various embodiments, are odor-controlling bodily fluid absorbent members. The odor-controlling bodily fluid absorbent members comprise an absorbent material and a halo active aromatic sulfonamide compound according to Formula (I), shown herein.

Formula (I)

wherein $R_1$, $R_2$, $R_3$, $R_4$, and $R_5$ are independently selected from hydrogen, COOH, $COOM_1$, COOR', $CON(R'')_2$, alkoxy, CN, $NO_2$, $SO_3R''$, halogen, substituted or unsubstituted phenyl, sulfonamide, halosulfonamide, and substituted or unsubstituted $C_1$-$C_{12}$ alkyl; $M_1$ is an alkali or alkaline earth metal; R' is substituted or unsubstituted $C_1$-$C_{12}$ alkyl; and R'' is hydrogen or substituted or unsubstituted $C_1$-$C_{12}$ alkyl, and the two R'' groups in $CON(R'')_2$ may be independently selected; wherein at least one of $R_1$, $R_2$, $R_3$, $R_4$, and $R_5$ is not hydrogen; X is halogen; M is an alkali or alkaline earth metal; and n is the number of water molecules per molecule of the sulfonamide compound.

The absorbent material may be a polymer or cellulosic fiber, such as wood fluff.

In embodiments, M may be sodium or potassium. Similarly, X may be chlorine, bromine, fluorine, or iodine.

In some particular embodiments, at least two of $R_1$, $R_2$, $R_3$, $R_4$, and $R_5$ are not hydrogen. In other embodiments, $R_3$ is methyl, COOH, or $COOM_1$. In still other embodiments, $R_3$ is methyl, COOH, or $COOM_1$; and at least one of $R_1$, $R_2$, $R_4$, and $R_5$ is not hydrogen.

In some embodiments, $R_3$ is chlorine, fluorine, $NO_2$, or methoxy. In other embodiments, $R_1$ is methyl or chlorine.

Additionally, the sulfonamide compound may have the structure of Formula (IV):

Formula (IV)

$*n\, H_2O$.

In other embodiments, $R_3$ is selected from COOH, $COOM_1$, COOR', $CON(R'')_2$, CN, $NO_2$, halogen, and substituted or unsubstituted $C_2$-$C_{12}$ alkyl.

In still other embodiments, $R_1$, $R_2$, $R_3$, $R_4$, and $R_5$ are independently selected from hydrogen, COOH, $COOM_1$, $NO_2$, halogen, and substituted or unsubstituted $C_1$-$C_{12}$ alkyl.

In some embodiments, $R_2$ and $R_4$ are identical to each other; and $R_1$, $R_3$, and $R_5$ are hydrogen. Alternatively, in some embodiments, $R_2$ and $R_4$ are hydrogen; and $R_1$, $R_3$, and $R_5$ are identical to each other.

In particular embodiments, $R_3$ is selected from COOH, $COOM_1$, COOR', and $CON(R'')_2$.

In specific embodiments, $R_1$, $R_2$, $R_3$, $R_4$, and $R_5$ are independently selected from hydrogen, COOH, $COOM_1$, COOR', $CON(R'')_2$, $NO_2$, halogen, and substituted or unsubstituted $C_1$-$C_{12}$ alkyl.

In other embodiments, $R_3$ is COOH or $COOM_1$; and $R_1$, $R_2$, $R_4$, and $R_5$ are independently selected from hydrogen, $NO_2$, halogen, and substituted or unsubstituted $C_1$-$C_{12}$ alkyl. In further specific embodiments, at least one of $R_1$, $R_2$, $R_4$, and $R_5$ is not hydrogen.

The odor-controlling bodily fluid absorbent member may also comprise a second different sulfonamide compound. The weight ratio of the two sulfonamide compounds may be from about 90:10 to about 10:90. In specific embodiments, one compound is N-chloro-p-carboxysulfonamide. The other compound may be N-chloro-p-toluenesulfonamide.

Alternatively, one of the two sulfonamide compounds may be of Formula (VI):

Formula (VI)

wherein $M_2$ is hydrogen, an alkali metal, or an alkaline earth metal.

The two sulfonamide compounds may be present in the range of from about 0.5 to about 15 weight percent, based on the weight of the absorbent member.

Generally, the sulfonamide compound can be present in the range of from about 0.5 to about 15 weight percent, based on the weight of the absorbent member, including from about 0.5 to about 1.5 weight percent or from about 7 to about 13 weight percent.

The odor-controlling bodily fluid absorbent member may further comprise a buffering agent.

Disclosed in other embodiments is a bodily fluid absorbent member, comprising: an absorbent material; and a halo active aromatic sulfonamide compound of Formula (I):

Formula (I)

wherein $R_1$, $R_2$, $R_4$, and $R_5$ are independently selected from hydrogen, COOH, $COOM_1$, COOR', $CON(R'')_2$, alkoxy, CN, $NO_2$, $SO_3R''$, halogen, substituted or unsubstituted phenyl, sulfonamide, halosulfonamide, and substituted or unsubstituted $C_1$-$C_{12}$ alkyl; $R_3$ is COOH, $COOM_1$, COOR', and $CON(R'')_2$; $M_1$ is an alkali or alkaline earth metal; R' is substituted or unsubstituted $C_1$-$C_{12}$ alkyl; and R" is hydrogen or substituted or unsubstituted $C_1$-$C_{12}$ alkyl, and the two R" groups in $CON(R'')_2$ may be independently selected; X is halogen; M is an alkali or alkaline earth metal; and n is the number of water molecules per molecule of the sulfonamide compound.

Again, M may be sodium or potassium, and X may be chlorine, bromine, fluorine, or iodine.

In some embodiments, at least one of $R_1$, $R_2$, $R_4$, and $R_5$ is not hydrogen.

In other embodiments, $R_1$, $R_2$, $R_4$, and $R_5$ are independently selected from hydrogen, COOH, $COOM_1$, $NO_2$, halogen, and substituted or unsubstituted $C_1$-$C_{12}$ alkyl.

In still other embodiments, $R_1$, $R_2$, $R_4$, and $R_5$ are independently selected from hydrogen, COOH, $COOM_1$, COOR', $CON(R'')_2$, $NO_2$, halogen, and substituted or unsubstituted $C_1$-$C_{12}$ alkyl.

In more specific embodiments, $R_1$, $R_2$, $R_4$, and $R_5$ are independently selected from hydrogen, $NO_2$, halogen, and substituted or unsubstituted $C_1$-$C_{12}$ alkyl.

The odor-controlling bodily fluid absorbent member may further comprise a second different halo active aromatic sulfonamide compound, such as N-chloro-p-toluenesulfonamide.

Also disclosed are processes for making an odor-controlling bodily fluid absorbent member. An absorbent material is provided and treated with a mixture. The absorbent material is subsequently shaped to form the absorbent member. The mixture comprises a halo active aromatic sulfonamide compound of Formula (I).

The mixture may be a solid or an aqueous solution. The absorbent material can be a polymer, cellulosic fiber, or a wood fluff.

In some processes, the absorbent material is provided and treated by applying the mixture to a sheet of wood fibers, and subsequently pulverizing the sheet to obtain the treated absorbent material.

Also disclosed are methods for controlling the odor of a bodily fluid. An odor-controlling bodily fluid absorbent member is provided that comprises an absorbent material and dispersed therein a halo active aromatic sulfonamide compound of Formula (I). The absorbent member is brought into contact with an odorific bodily fluid to allow the sulfonamide compound to neutralize odor-causing molecules present in the bodily fluid.

These and other non-limiting features or characteristics of the present disclosure will be further described below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

A more complete understanding of the components, processes, and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The modifier "about" used in connection with a quantity is inclusive of the stated value and has the meaning dictated by the context (for example, it includes at least the degree of error associated with the measurement of the particular quantity). In addition, the value or range endpoints so modified should also be considered as being disclosed. For example, the range "about 2 to about 4" should also be considered as disclosing the range "2 to 4".

Halo active aromatic sulfonamide organic compounds are known. Chloramine-T is an example of a sulfonamide organic compound which has been used in many applications. The usefulness of Chloramine-T is predicated on its ability to release an active Cl+ ion when needed on demand, immediately after which, it simultaneously generates an active aromatic sulfo nitrene companion ion. The active Cl+ ion and the companion aromatic sulfo nitrene ion may work together to degrade odor-causing molecules. The term "Cl+" refers to the fact that the chlorine atom has a +1 formal charge in a hypochlorite ion, ClO⁻, which is the form taken by the chlorine atom when dissociated from the sulfonamide compound. A chlorine atom is generally considered to have a charge of 1⁻. Reference to the chlorine atom as having a +1 or 1⁻ charge may be used in this application interchangeably because this terminology has no effect on the compound itself or its use.

Most odor causing molecules are mercaptans, sulfides heterocyclic or amine based compounds. Halo active aromatic sulfonamide compounds are excellent agents for eliminating odors from these classes of compounds as both the Cl+ cations and the sulfonamide moiety remaining after the Cl+ cations are produced, react with the odor causing molecule(s).

The odor-controlling bodily fluid absorbent members of the present disclosure generally comprise (i) a absorbent material or substrate; and (ii) a halo active aromatic sulfonamide compound, as described further herein. The absorbent material or substrate is treated with the sulfonamide compound, or in other words, the sulfonamide compound is generally dispersed within or throughout the absorbent material. The absorbent material is then shaped to form the absorbent member. The absorbent member may be used in, for example, a diaper or other sanitary product.

The shape of the odor-controlling bodily fluid absorbent member can be varied depending on its use; for example, it can be made as a flat sheet or in a tubular form. It should be noted that the absorbent member is generally only one part of the overall consumer article.

Figure 1:
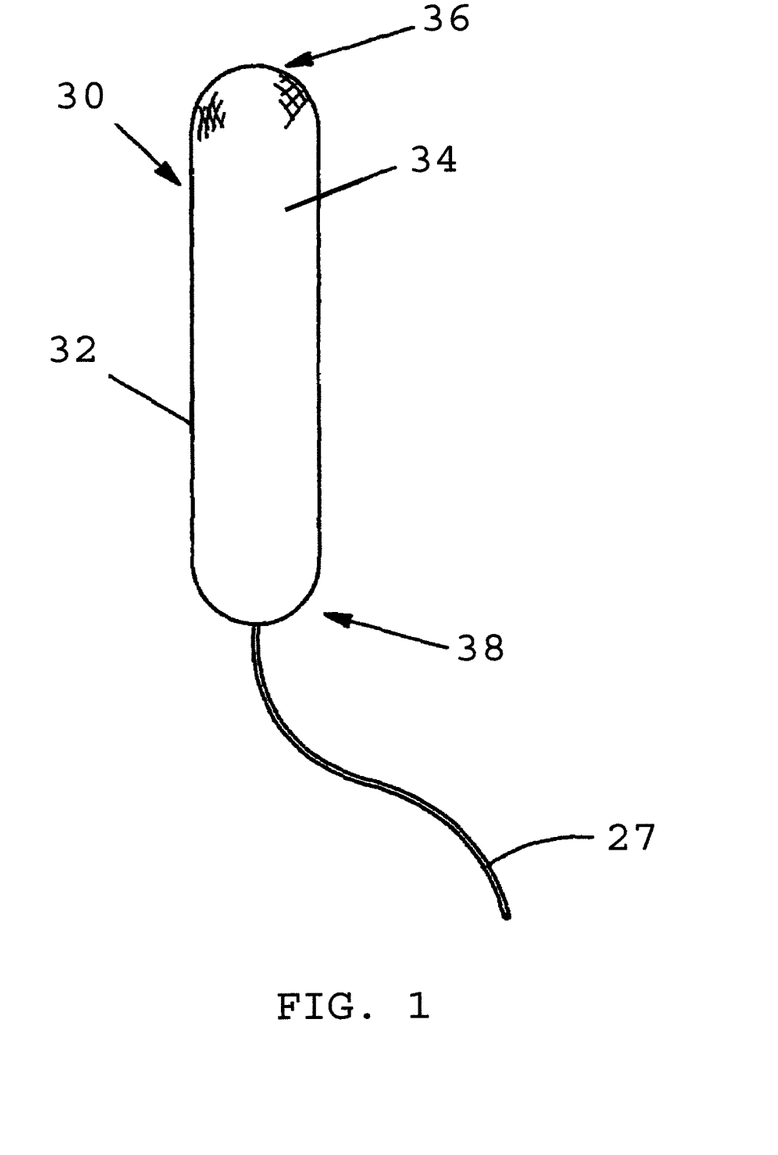
FIG. 1 is a side view of a tampon formed from an absorbent member of the present disclosure.

For example, the absorbent member may be used to form a tampon. Referring to FIG. 1, the tampon 30 comprises an absorbent member 32 which has been compressed or shaped into a tube. Prior to compression, the absorbent member may have any suitable size and thickness suitable for compression into a tampon having a vaginally insertable shape. The absorbent member is generally square or rectangular prior to compression. A typical size for the absorbent member prior to compression may be from about 40 mm to about 100 mm in length and from about 40 mm to about 80 mm in width. The absorbent member 22 has an exterior surface 34, and an insertion end 36 opposed to a withdrawal end 38. A withdrawal means, such as string 27, extends from the withdrawal end 38. The withdrawal means can take on other forms such as a ribbon, loop, tab, or the like, and may be attached in any suitable manner known in the art including sewing, adhesive attachment, or a combination of known bonding methods. The withdrawal means may be joined to any suitable location on the tampon.

Figure 2:
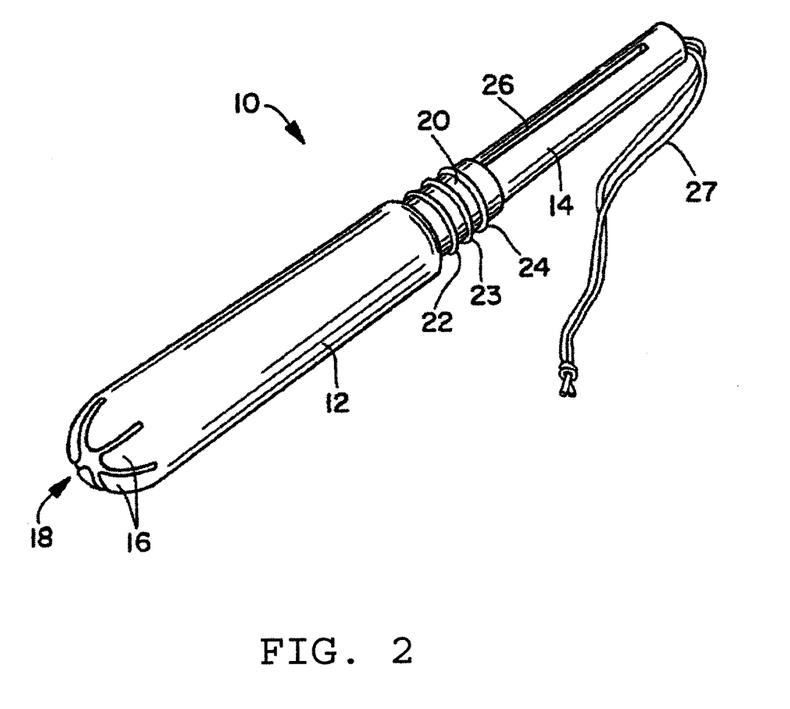
FIG. 2 is a perspective view of a tampon applicator.

The tampon may be inserted digitally or through the use of an applicator. Such applicators typically have a "tube and plunger" type arrangement and may be plastic, paper, or other suitable material. Additionally, a "compact" type applicator is also suitable. Referring to FIG. 2, a compact tampon applicator 10 is shown having an outer tube 12 and an inner tube 14. The outer tube 12 has a series of petals 16 formed at a forward end 18 which is designed to be inserted into a woman's vagina. The outer tube 12 is provided with a gripping portion 20 that includes ridges 22, 23 and 24. The inner tube 14 has an elongated slot 26 that aids in retaining the inner tube 14 in the outer tube 12. The cut-out slot 26 also aids in moving the inner tube 14 relative to the outer tube 12 during use. A withdrawal string 27 is attached to one end of a hollow tampon 28 and extends through the inner tube 14. The withdrawal string 27 is used to withdraw the tampon 28 from the vagina after use. Here, the final article is a tampon with applicator.

Figure 3:
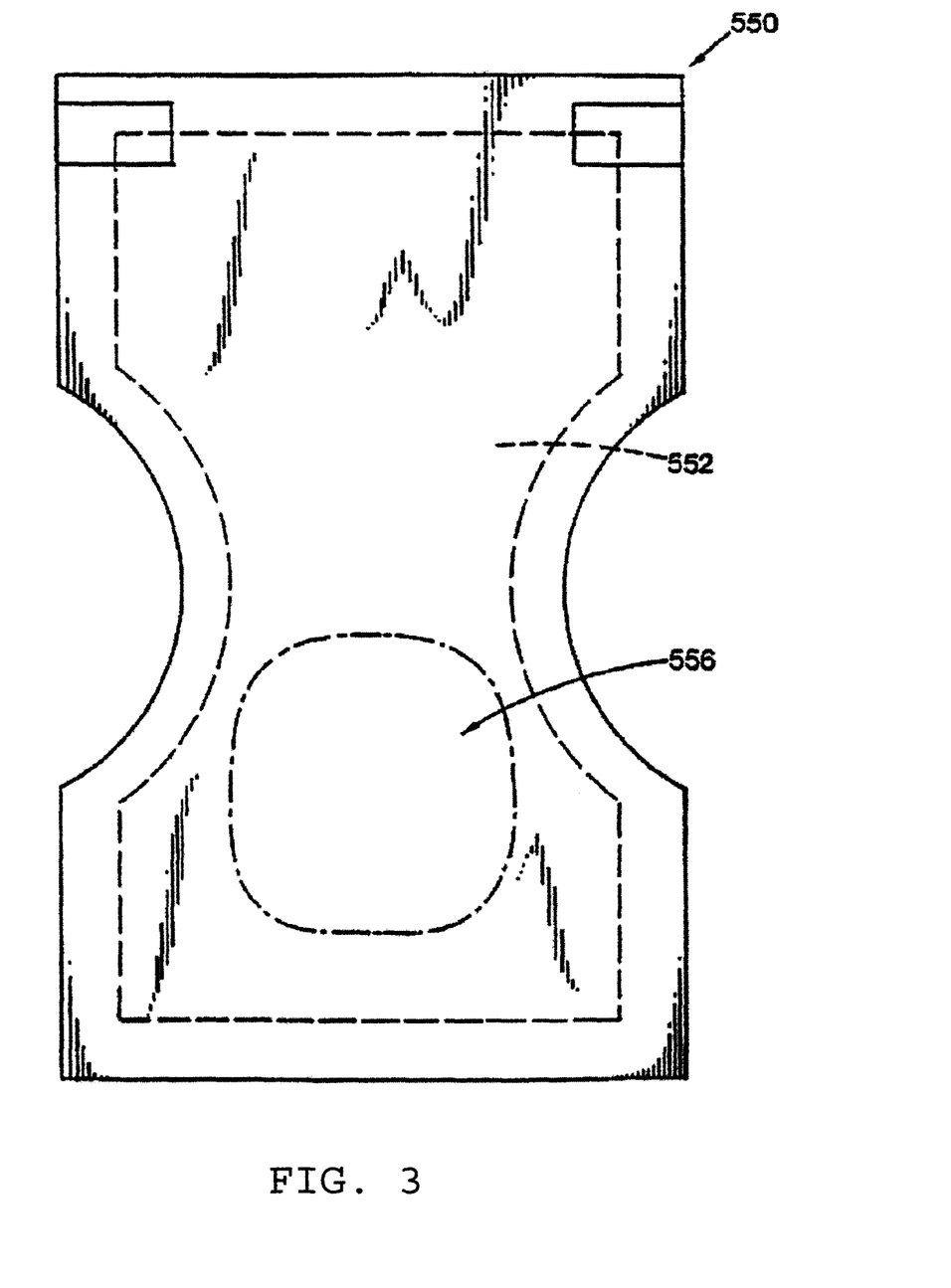
FIG. 3 is a top view of a diaper containing an absorbent member of the present disclosure.

As another example, FIG. 3 illustrates a conventional disposable diaper 550. The diaper includes a liner 554. The absorbent member may be in the shape of a flat sheet, and either be attached to a top side of the liner or inserted into the liner. The absorbent member may be shaped to cover the majority of the liner, as indicated at 552. Alternatively, the absorbent member may be shaped to fit a target zone, for example, the crotch portion of a diaper indicated at 556. Here, the final article is a diaper. Generally speaking, the absorbent member may be engaged with a housing to form a final article.

The absorbent material or substrate may be natural or synthetic. The absorbent material may also be in the form of fibers, powders, or granules, or in larger amounts in the form of sheets, mats, pads, or tubes. Exemplary absorbent materials may include synthetic fibers made from polyacrylates, polyacrylamide copolymers, ethylene maleic anhydride copolymers, polyvinyl alcohol copolymers, cross-linked polyethylene oxide, starch grafted copolymers of polyacrylonitrile, and cellulosic fibers such as cotton, rayon, and wood pulp. In specific embodiments, the absorbent material is a "fluff" made by pulverizing sheets of wood pulp fibers. Additionally, the absorbent materials may be pretreated with surfactants, wetting agents to enhance their wettability, or with antimicrobial agents, pigments, etc.

The halo active aromatic sulfonamide compound has the structure of Formula (I):

Formula (I)

wherein $R_1$, $R_2$, $R_3$, $R_4$, and $R_5$ are independently selected from hydrogen, COOH, $COOM_1$, COOR', $CON(R'')_2$, alkoxy, CN, $NO_2$, $SO_3R''$, halogen, substituted or unsubstituted phenyl, sulfonamide, halosulfonamide, and substituted or unsubstituted $C_1$-$C_{12}$ alkyl;

wherein at least one of $R_1$, $R_2$, $R_3$, $R_4$, and $R_5$ is not hydrogen;

X is halogen;

M is an alkali or alkaline earth metal; and n is the number of water molecules per molecule of the sulfonamide compound.

$M_1$ is also an alkali or alkaline earth metal, and need not be the same as M, though generally M and $M_1$ are the same. Generally, M is sodium or potassium. X is generally chlorine, bromine, fluorine, or iodine, and in particular embodiments is chlorine. Compounds of Formula (I) may or may not be hydrated, as indicated by the variable n. In particular embodiments, the compounds of Formula (I) are a trihydrate (i.e., n=3). In other embodiments, the compound is in a solid form, such as a powder.

R' is substituted or unsubstituted $C_1$-$C_{12}$ alkyl. R" is hydrogen or substituted or unsubstituted $C_1$-$C_{12}$ alkyl, and the two R" groups in the $CON(R")_2$ may be independently selected.

When the phenyl and/or alkyl group is substituted, one or more hydrogen atoms may be independently replaced with hydroxyl or halogen.

In some embodiments of Formula (I), at least two of $R_1$, $R_2$, $R_3$, $R_4$, and $R_5$ are not hydrogen.

In particular embodiments of Formula (I), $R_3$ is methyl, COOH, or $COOM_1$; $R_1$, $R_2$, $R_4$, and $R_5$ are independently selected from hydrogen, COOH, $COOM_1$, COOR', $CON(R")_2$, alkoxy, CN, $NO_2$, $SO_3R"$, halogen, substituted or unsubstituted phenyl, sulfonamide, halosulfonamide, and substituted or unsubstituted $C_1$-$C_{12}$ alkyl; X is halogen; $M_1$ is an alkali or alkaline earth metal; and n is the number of water molecules per molecule of the sulfonamide compound.

In further embodiments, $R_3$ is methyl, COOH, or $COOM_1$; $R_1$, $R_2$, $R_4$, and $R_5$ are independently selected from hydrogen, COOH, $COOM_1$, COOR', $CON(R")_2$, alkoxy, CN, $NO_2$, $SO_3R"$, halogen, substituted or unsubstituted phenyl, sulfonamide, halosulfonamide, and substituted or unsubstituted $C_1$-$C_{12}$ alkyl; X is halogen; M is an alkali or alkaline earth metal; n is the number of water molecules per molecule of the sulfonamide compound; and at least one of $R_1$, $R_2$, $R_4$, and $R_5$ is not hydrogen.

In other embodiments of Formula (I), the halo active aromatic sulfonamide compound has the structure of Formula (II):

Formula (II)

wherein $R_3$ is chlorine, fluorine, $NO_2$, or methoxy; X is halogen; M is an alkali or alkaline earth metal; n is the number of water molecules per molecule of the sulfonamide compound.

In other embodiments of Formula (I), the halo active aromatic sulfonamide compound has the structure of Formula (III):

Formula (III)

wherein $R_1$ is methyl or chlorine; X is halogen; M is an alkali or alkaline earth metal; n is the number of water molecules per molecule of the sulfonamide compound.

In one specific embodiment, the halo active aromatic sulfonamide compound has the structure of Formula (IV):

Formula (IV)

In yet other embodiments of Formula (I), $R_3$ is selected from COOH, $COOM_1$, COOR', $CON(R")_2$, CN, $NO_2$, halogen, and substituted or unsubstituted $C_2$-$C_{12}$ alkyl; $R_1$, $R_2$, $R_4$, and $R_5$ are independently selected from hydrogen, COOH, $COOM_1$, COOR', $CON(R")_2$, alkoxy, CN, $NO_2$, $SO_3R"$, halogen, substituted or unsubstituted phenyl, sulfonamide, halosulfonamide, and substituted or unsubstituted $C_1$-$C_{12}$ alkyl; X is halogen; M is an alkali or alkaline earth metal; and n is the number of water molecules per molecule of the sulfonamide compound.

In still other embodiments of Formula (I), $R_1$, $R_2$, $R_3$, $R_4$, and $R_5$ are independently selected from hydrogen, COOH, $COOM_1$, $NO_2$, halogen, and substituted or unsubstituted $C_1$-$C_{12}$ alkyl; X is halogen; M is an alkali or alkaline earth metal; and n is the number of water molecules per molecule of the sulfonamide compound.

In yet other embodiments of Formula (I), $R_2$ and $R_4$ are identical to each other; and $R_1$, $R_3$, and $R_5$ are hydrogen.

In yet other embodiments of Formula (I), $R_2$ and $R_4$ are hydrogen; and $R_1$, $R_3$, and $R_5$ are identical to each other.

In more specific embodiments of Formula (I), $R_3$ is selected from COOH, $COOM_1$, COOR', and $CON(R")_2$. Most desirably, $R_3$ is COOH or $COOM_1$, while $R_1$, $R_2$, $R_4$, and $R_5$ are hydrogen.

In other embodiments of Formula (I), $R_1$, $R_2$, $R_3$, $R_4$, and $R_5$ are independently selected from hydrogen, COOH, $COOM_1$, COOR', $CON(R")_2$, $NO_2$, halogen, and substituted or unsubstituted $C_1$-$C_{12}$ alkyl; wherein at least one of $R_1$, $R_2$, $R_3$, $R_4$, and $R_5$ is not hydrogen; X is halogen; M is an alkali or alkaline earth metal; and n is the number of water molecules per molecule of the sulfonamide compound.

In still other embodiments of Formula (I), $R_3$ is COOH or $COOM_1$; $R_1$, $R_2$, $R_4$, and $R_5$ are independently selected from hydrogen, $NO_2$, halogen, and substituted or unsubstituted $C_1$-$C_{12}$ alkyl; X is halogen; M is an alkali or alkaline earth metal; and n is the number of water molecules per molecule of the sulfonamide compound. In further specific embodiments, at least one of $R_1$, $R_2$, $R_4$, and $R_5$ is not hydrogen.

In some embodiments, the absorbent member may contain two different sulfonamide compounds. In particular, the sulfonamide compounds differ in properties such as odor-controlling ability, stability, and cost. It may be desirable to use a mixture of two or more compounds rather than just one compound in the absorbent member to balance odor-controlling properties with economic factors such as cost and availability of the sulfonamide compounds. For example, each sulfonamide compound may have a different reaction rate, stability, and/or release rate, or neutralize different odor-causing molecules more efficiently. The weight ratio between the two sulfonamide compounds may range from about 90:10 to about 10:90, or from about 70:30 to about 30:70. In some embodiments, one of the sulfonamide compounds is of Formula (I); in other embodiments, both sulfonamide compounds are of Formula (I).

In specific embodiments, the two sulfonamide compounds are N-chloro-p-toluenesulfonamide (i.e. chloramine-T) and N-chloro-p-carboxysulfonamide. These two compounds are shown below as Formulas (V) and (VI):

wherein $M_2$ is hydrogen or $M_1$, as defined above; X is halogen, M is an alkali or alkaline earth metal; and n is the number of water molecules per molecule of the sulfonamide compound. Desirably, $M_2$ is hydrogen, sodium, or potassium. In other embodiments, one of the compounds present is the N-chloro-p-carboxysulfonamide of Formula (VI).

The halo active aromatic sulfonamide compounds of Formula (I) are stable and do not decompose in aqueous solution, allowing the absorbent member to have a long shelf life. The compounds of Formula (I) are also very soluble in water, low in toxicity, and have minimal bleach odor.

The sulfonamide compound(s) of Formula (I) may be present in the absorbent member in the range of from about 0.1 to about 50 weight percent, based on the weight of the absorbent member. In more specific embodiments, the sulfonamide compound(s) are present in the range of from about 0.5 to about 15 weight percent, from about 0.5 to about 1.5 weight percent, or from about 4 to about 7.5 weight percent.

For stability and for optimum performance, the pH of the absorbent member should be between 6 and 14, though generally the pH should be kept between 8 and 9.5, or from 8.5 to 9. As urine can have a pH ranging from 4.5 to 8, and is generally acidic, this pH range also helps to neutralize the urine collected in the sanitary product.

In order to maintain the solution within these pH ranges, a buffering agent may be added to the absorbent member. The buffering agent can compensate for any change in pH that may result from the acidity of the urine, the conditions of application, the type of absorbent material or substrate, and/or the nature of the odor causing molecule. Exemplary buffering agents include sodium bicarbonate, potassium bicarbonate, sodium carbonate, potassium carbonate, acetate buffers (such as sodium acetate), phosphate buffers (such as tri and di sodium phosphate and mixtures thereof, pH blended phosphates, sulfate buffers (such as di and tri sodium sulfate), and mixtures thereof. The buffering agent can be added up to the limit of solubility. The preferred range for the concentration of the buffering agent is from about 5% to about 200% by weight of the active compound in solution, including from about 5% to about 50% or from about 25% to about 50%. Preferred buffering agents are potassium and sodium biocarbonate.

A low molecular weight alcohol may also be added to the absorbent member to enhance the activity of the sulfonamide compound. An exemplary alcohol is t-butanol. The alcohol may have several effects. The alcohol enhances the odor removal activity of the active aromatic N-halo sulfonamide group. The alcohol can also increase surface activity or enable the use of a more favorable blend of fragrances, surface active compounds and the like. The type of alcohol used, however, is somewhat limited. T-butanol or related tertiary alcohols are preferred because they do not contain hydrogen atoms alpha to the oxygen alcohol moiety, and allow for greater stability. The alpha hydrogen atoms apparently detract from stability due to interaction with the active halogen contained in the active aromatic halo sulfonamide compound. However, at pH>10, alcohols containing alpha hydrogen atoms, such as ethanol and isopropanol, were found to not affect stability.

The alcohol can be present at concentrations of from about 0.1 to about 80 weight percent of the absorbent material, including from about 0.1 to about 2.0 weight percent and especially from about 0.2 to about 1.0 weight percent.

A surfactant, or wetting agent, can also be added to the odor-controlling bodily fluid absorbent member. The surfactant decreases surface tension, allowing the sulfonamide compound to be more easily activated when contacted by the bodily fluid. Both non-ionic and anionic surfactants can be used. However, in specific embodiments, a surfactant is not used.

The halo active aromatic sulfonamide compounds of Formula (I) can be added to the absorbent material using known methods. In particular, when the absorbent material is wood fluff, the sulfonamide compound can be added prior to fluffing when the wood is still in the form of a sheet of wood fibers, or the sulfonamide compound can be added after fluffing has occurred and the wood is in the form of a fibrous, cotton-like material. The sulfonamide compound can be impregnated into or dispersed throughout the absorbent material.

Generally, the sulfonamide compound is applied as a mixture. For example, the compound may be mixed with water or another liquid to form an aqueous or other solution. The solution is usually made of one or more sulfonamide compounds in a buffered formulation, up to the saturation point in solution of the compound(s). This may range from 5% to 25% by weight in aqueous solution, depending on the solubility of the compound and the solvent (alcohol or other). The solution is then sprayed on the absorbent material. The solvent is then allowed to evaporate, leaving behind the active sulfonamide compound. Multiple sprays can be used to increase the amount of active sulfonamide compound on the absorbent material.

Alternatively, the sulfonamide compound can be used in a solid form, such as a powder. The sulfonamide compound in its solid form can be mixed with other solid additives as well, such as the buffering agent, a binder, etc. The use of trace amounts of compatible perfume additives is also contemplated.

The odor-controlling bodily fluid absorbent members of the present disclosure are useful for controlling odor in sanitary products such as diapers, sanitary napkins, etc, or as wipes for general use (i.e. as a thin flat sheet). The absorbent members are also useful in products such as wound dressings, bandages, etc. Generally, the absorbent member is contacted with the bodily fluid, and the sulfonamide compound neutralizes odor-causing molecules in the bodily fluid. For example, the absorbent member may be located in a diaper, and urine or feces subsequently contact the absorbent member. Alternatively, the absorbent member is part of a bandage which is applied to a wound that oozes pus, and the absorbent member contacts the pus.

An exemplary odor-controlling bodily fluid absorbent member includes absorbent material, the two sulfonamide compounds of Formulas (V) and (VI) in a weight ratio of about 1:2, sodium bicarbonate, 0.50% t-butanol, and a trace of fragrance.

The bodily fluid absorbent members of the present disclosure are illustrated by the following non-limiting examples, it being understood that these examples are intended to be illustrative only and that the present application is not intended to be limited to the materials, conditions, process parameters and the like recited herein. All proportions are by weight unless otherwise indicated.

FIRST SET OF EXAMPLES

Odor-controlling bodily fluid absorbent members were made from wood fluff. The wood fluff was treated with one of three different combinations of sulfonamide compounds. Combination A contained approximately 70% N-chloro-p-carboxysulfonamide (shown below as Formula (VIII) and 30% chloramine-T (shown below as Formula (VII)). Combination B was only N-chloro-p-carboxysulfonamide, and Combination C was only chloramine-T. The combinations were sprayed on as aqueous solutions containing either 0.5 wt %, 1.0 wt %, or 1.5 wt % of the sulfonamide compound(s).

Formula (VII)

Formula (VIII)

Example 1

Here, a wood fluff ball approximately two to three inches in diameter was sprayed with red fox urine (a very smelly substance), then sprayed with different odor control formulations to see how efficient the formulation was at eliminating the odor. A control wood fluff ball was not sprayed with any odor control formulations.

All subjects that smelled the control ball versus the treated balls marked extremely notable differences, with some saying the odor was completely gone and not detectable.

The test was repeated with human urine from a 5 year old female. Again, the test formulations did very well at eliminating the odor.

Example 2

Pressed fiber wood sheets having a size of 18 inches by 2 inches were sprayed with Solution A, B, or C. The weight of the wood sheet before spraying was measured, and the weight of the wood sheet was then measured again 24 hours after spraying to determine the amount of sulfonamide compound present on the wood sheet.

The wood sheet was then converted to wood fluff by pulverizing. Table 1 below lists the 15 different samples, indicating which solution was used and the resulting amount of sulfonamide compound present.

TABLE 1

| Sample | Combination | weight before spraying (g) | weight 24 hours after spraying (h) | weight of sulfonamide (g) | wt % sulfonamide |
|---|---|---|---|---|---|
| A-1 | A | 17.1 | 17.5 | 0.4 | 2.3% |
| A-2 | A | 17.3 | 17.6 | 0.3 | 1.7% |
| B-1 | A | 17.5 | 17.7 | 0.2 | 1.1% |
| B-2 | A | 16.8 | 16.9 | 0.1 | 0.6% |
| C-1 | A | 17.6 | 17.8 | 0.2 | 1.1% |
| C-2 | A | 17.9 | 18.2 | 0.3 | 1.6% |
| D-1 | B | 17   | 18.3 | 1.3 | 7.1% |
| D-2 | B | 17.7 | 19.2 | 1.5 | 7.8% |
| E-1 | B | 17.6 | 20.1 | 2.5 | 12.4% |
| E-2 | A | 17.1 | 17.2 | 0.1 | 0.6% |
| F-1 | C | 18.1 | 18.2 | 0.1 | 0.5% |
| F-2 | C | 17.7 | 17.9 | 0.2 | 1.1% |
| F-3 | C | 17.3 | 17.4 | 0.1 | 0.6% |
| G-1 | C | 17.6 | 18   | 0.4 | 2.2% |
| G-2 | C | 17.5 | 17.9 | 0.4 | 2.2% |

Some of the wood fluff samples were then sprayed with red fox urine, and smelled by three subjects. Subject T first smelled the fluff that had been treated, then smelled the control fluff. Subject J smelled the treated fluff approximately 15 minutes after spraying with red fox urine, then smelled the control fluff. Subject D first smelled the control fluff, then smelled the treated fluff approximately 20 minutes after spraying. Their evaluations are listed below in Table 2 on a scale of 0 to 10, with 0 indicating no odor and 10 indicating an overwhelming odor.

TABLE 2

| Sample | Combination | wt % sulfonamide | Subject T (0 min) | Subject J (15 min) | Subject D (20 min) |
|---|---|---|---|---|---|
| A-1 | A | 2.3% | 1 | 1 | 5 |
| A-2 | A | 1.7% |   |   |   |
| B-1 | A | 1.1% | 2 | 0 | 3 |
| B-2 | A | 0.6% |   |   |   |
| C-1 | A | 1.1% | 0 | 0 | 0 |
| C-2 | A | 1.6% |   |   |   |
| D-1 | B | 7.1% | 1 | 1 | 1 |
| D-2 | B | 7.8% |   |   |   |
| E-1 | B | 12.4% | 1 | 1 | 1 |
| E-2 | A | 0.0% | 1 | 2 | 1 |
| F-1 | C | 0.0% | 8 | 3 | 8 |
| F-2 | C | 1.1% | 8 | 1 | 8 |

TABLE 2-continued

| Sample | Combination | wt % sulfonamide | Subject T (0 min) | Subject J (15 min) | Subject D (20 min) |
|---|---|---|---|---|---|
| F-3 | C | 0.6% | 1 | 2 | 1 |
| G-1 | C | 2.2% | 4 | 1 | 4 |
| G-2 | C | 2.2% | 3 | 0 | 3 |

This quick evaluation showed that Examples C-1, D-1, and E1 worked best at eliminating the odor from the red fox urine. Of course, every individual's olfactory sense is different, and Subject J's divergent numbers in F-1, F2, and G-1 may be due to the fact that Subject J did not smell the control fluff first and therefore did not expect what a 10 would be.

SECOND SET OF EXAMPLES

An aqueous solution was made that contained 4.5 wt % N-chloro-p-carboxysulfonamide, 1.5 wt % sodium bicarbonate, and 94 wt % water. Next, a wood fiber sheet having dimensions of 10 inches×20 inches was prepared. The wood fiber sheet was 92-95% dry, and had a weight of 99 to 100 grams. 78 grams of the aqueous solution was then added to only the top side of the wood fiber sheet. After the aqueous solution was dried, the wood fiber sheet was tested and then fluffed in a pulverizer.

The present disclosure has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. An odor-controlling bodily fluid absorbent member, comprising:
   an absorbent material; and dispersed therein
   a first halo active aromatic sulfonamide compound of Formula (I):

Formula (I)

wherein $R_1$, $R_2$, $R_4$, and $R_5$ are independently selected from hydrogen, COOH, COOM$_1$, COOR', CON(R")$_2$, alkoxy, CN, NO$_2$, SO$_3$R", halogen, substituted or unsubstituted phenyl, sulfonamide, halosulfonamide, and substituted or unsubstituted C$_1$-C$_{12}$ alkyl; M$_1$ is an alkali or alkaline earth metal; R' is substituted or unsubstituted C$_1$-C$_{12}$ alkyl; and R" is hydrogen or substituted or unsubstituted C$_1$-C$_{12}$ alkyl, and the two R" groups in CON(R")$_2$ may be independently selected;
wherein $R_3$ is selected from COOH, COOM$_1$, COOR', and CON(R")$_2$;
X is halogen;
M is an alkali or alkaline earth metal; and
n is the number of water molecules per molecule of the sulfonamide compound; and
wherein the first halo active aromatic sulfonamide compound is present in the range of from about 0.5 to about 15 weight percent, based on the weight of the absorbent member; and
wherein the absorbent member does not comprise chloramine-T.

2. The absorbent member of claim 1, wherein the absorbent material is a polymer, cellulosic fiber, or a wood fluff.

3. The absorbent member of claim 1, wherein $R_2$ and $R_4$ are hydrogen; and $R_1$, $R_3$, and $R_5$ are identical to each other.

4. The absorbent member of claim 1, wherein $R_3$ is COOH or COOM$_1$; and $R_1$, $R_2$, $R_4$, and $R_5$ are independently selected from hydrogen, NO$_2$, halogen, and substituted or unsubstituted C$_1$-C$_{12}$ alkyl.

5. The absorbent member of claim 1, wherein the first halo active aromatic sulfonamide compound is N-chloro-p-carboxysulfonamide.

6. The absorbent member of claim 1, further comprising a buffering agent or an alcohol.

7. The absorbent member of claim 1, wherein the absorbent member is used in a diaper, a sanitary napkin, a tampon, a wound dressing, or a bandage.

8. The absorbent member of claim 1, wherein the absorbent member further comprises a second different sulfonamide compound.

9. The absorbent member of claim 8, wherein the two sulfonamide compounds are present in the range of from about 0.1 to about 50 weight percent, based on the weight of the absorbent member.

10. The absorbent member of claim 1, wherein the first halo active aromatic sulfonamide compound is present in the range of from about 4 to about 7.5 weight percent, based on the weight of the absorbent member.

11. The absorbent member of claim 1, wherein the absorbent member consists of the absorbent material and the first halo active aromatic sulfonamide compound.

12. The absorbent member of claim 8, wherein the absorbent member consists of the absorbent material, the first halo active aromatic sulfonamide compound, and the second different sulfonamide compound.

13. The absorbent member of claim 1, further comprising: t-butanol.

14. The absorbent member of claim 1, wherein the first halo active aromatic sulfonamide compound is present in the range of from about 0.5 to about 1.5 wt %, based on the weight of the absorbent member.

15. The absorbent member of claim 1, wherein the first halo active aromatic sulfonamide compound is present in the range of from about 7 to about 13 wt %, based on the weight of the absorbent member.

16. The absorbent member of claim 8, wherein a weight ratio of the first halo active aromatic sulfonamide compound to the second different sulfonamide compound is from 90:10 to 10:90.

17. The absorbent member of claim 8, wherein a weight ratio of the first halo active aromatic sulfonamide compound to the second different sulfonamide compound is from 70:30 to 30:70.

18. The absorbent member of claim 8, wherein the two sulfonamide compounds are present in the range of from about 0.5 to about 15 weight percent, based on the weight of the absorbent member.

19. The absorbent member of claim 8, wherein the two sulfonamide compounds are present in the range of from about 0.5 to about 1.5 weight percent, based on the weight of the absorbent member.

20. The absorbent member of claim 8, wherein the two sulfonamide compounds are present in the range of from about 4 to about 7.5 weight percent, based on the weight of the absorbent member.

* * * * *